United States Patent [19]

Sanuki

[11] Patent Number: 5,199,857
[45] Date of Patent: Apr. 6, 1993

[54] DUAL PLUNGER PUMP SYSTEM
[75] Inventor: Sannosuke Sanuki, Tokyo, Japan
[73] Assignee: Sanuki Kogyo Co., Ltd., Tokyo, Japan
[21] Appl. No.: 845,318
[22] Filed: Mar. 3, 1992
[30] Foreign Application Priority Data
  Mar. 15, 1991 [JP] Japan .................. 3-75828
[51] Int. Cl.$^5$ .......................... F04B 9/00; F04B 39/00; F04B 49/00; F04B 45/00
[52] U.S. Cl. .................................. 417/319; 417/223; 417/435
[58] Field of Search ................ 417/319, 223, 435, 429
[56] References Cited
U.S. PATENT DOCUMENTS
  4,392,784  7/1983  Hanafi ............................. 417/435
  4,416,588 11/1983  Karliner ........................... 417/319

FOREIGN PATENT DOCUMENTS
  0444387  9/1991  European Pat. Off. ............ 417/319

Primary Examiner—Richard A. Bertsch
Assistant Examiner—Alfred Basichas
Attorney, Agent, or Firm—Armstrong, Westerman, Hattori, McLeland & Naughton

[57] ABSTRACT

Two plungers in the dual plunger pumps are selectively operated by either short-stroke cams or long-stroke cams which are disposed on a rotary drive shaft. When rotating the rotary drive shaft in one direction, the long-stroke cams are driven to operate the plungers with a large stroke. When the drive shaft rotates in the reverse direction, the long-stroke cams run idle by way of a one-way clutch disposed between the drive shaft and the long-stroke cams, while the short-stroke cams are driven to operate the plungers with a small stroke.

2 Claims, 4 Drawing Sheets

DUAL PLUNGER PUMP SYSTEM

BACKGROUND OF THE INVENTION

1. Field of the Invention

This invention relates to a dual plunger pump system for use in, for example, a flow-injection analyzer and a fluid analyzer used in a fluid chromatographic device.

2. Description of the Prior Art

Generally, fluid flowing through a fluid analyzer employed in a fluid chromatographic device should be supplied thereto without causing any pulsating flow in order to be measured with a high accuracy. Therefore, the conventional fluid analyzer of an old type has been provided with the so-called damper mechanism using air pressure. Recently, there has been proposed the dual plunger pump system of the latest type using two plungers which are alternately reciprocated in plunger cylinders for introducing the fluid into one conduit so as to prevent the pulsating flow of fluid. (Japanese Patent Application Public Disclosure SHO 56-98582(A) and Japanese Utility Model Registration Application Public Disclosure SHO 61-32950(A))

Also in a case of combining luminescent reagents or other reacting reagents with each other to be reacted in the conduit in the aforesaid fluid analyzer, the dual plunger pump system has been used for alternately introducing two kinds of reagents to be combined into one conduit by the reciprocations of the respective plungers in the pump. In this case, the smaller the amount of the fluid supplied by one reciprocating stroke of the plunger is, the more the efficiency of combining the reagents increases. Thus, there are being used a dual plunger pump system of the trace-quantity supplying type in which the reciprocating stroke of each plunger is made small.

In the trace-quantity supplying type dual plunger pump system as above, since the volume of the plunger cylinder per one reciprocating stroke of the plunger is small, the change of pressure in the conduit into which the fluid is fed is small, causing evolution of air bubbles tending to be adhered to the interior of a check valve used in the pump. The air bubbles have a function of absorbing the pressure produced by the reciprocating plunger, thereby preventing the fluid from being sent through the conduit.

In order to solve the problem noted above, there has been so far used a plunger pump system as shown in FIG. 6, in which a change valve 2 is connected to the discharge pipes 3a and 3b of plunger pumps 1a and 1b so that the discharge pipes 3a and 3b can be alternatively connected freely to either conflux passages 4a and 4b or scavenging-deaerating passages 5a and 5b. To the scavenging-deaerating passages 5a and 5b, there are connected high-volume manual suction pumps 6a and 6b so as to be manually operated for cleansing the interior of the plunger pumps 1a and 1b while removing the air bubbles in the plunger pumps at the beginning of operation.

As noted above, the conventional dual plunger pump system calls for the onerous works for scavenging and deaerating, which are manually performed at the outset each time different fluid samples are dealt with. The scavenging and deaerating works could not be automatized and have entailed a disadvantage such that the conventional dual plunger pump system cannot be applied to a fluid analyzer capable of dealing with a great quantity of fluid, which has appeared with progress in medical science.

SUMMARY OF THE INVENTION

This invention is made to solve the problems described above and provides a dual plunger pump system capable of automatically carrying out scavenging and deaerating works which are required prior to analysis of fluid to be dealt with, and sending out continuously even a very small amount of fluid to be analyzed.

To attain the object described above according to this invention, there is provided a dual plunger pump system which comprises a pair of cylinders, a pair of plungers disposed within the cylinders, a pair of short-stroke cams for alternately operating the plungers, a rotary drive shaft for retaining the short-stroke cams, a pair of long-stroke cams opposite to the respective plungers, and a one-way clutch which is freely rotatable relative to the rotary drive shaft and disposed between the long-stroke cams and the rotary drive shaft so that rotary motion of the rotary drive shaft can be transmitted to the long-stroke cams only when the rotary drive shaft is driven in one direction.

The dual plunger pump system of this invention can send out continuously a very small amount of fluid alternately from the cylinders by reciprocating the plungers by use of the short-stroke cams when rotating the rotary drive shaft in the direction in which the rotary motion of the rotary drive shaft is not transmitted to the long-stroke cams. When the rotary drive shaft is driven in the reverse direction, the long-stroke cams are rotated through the one-way clutch, so that the plungers are reciprocated by the long-stroke cams to send out a large quantity of fluid.

Other and further objects of this invention will become obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The other objects and features of the present invention will be hereinafter explained in detail with reference to the accompanying drawings, wherein.

DESCRIPTION OF THE PREFERRED EMBODIMENT

Figure 1:
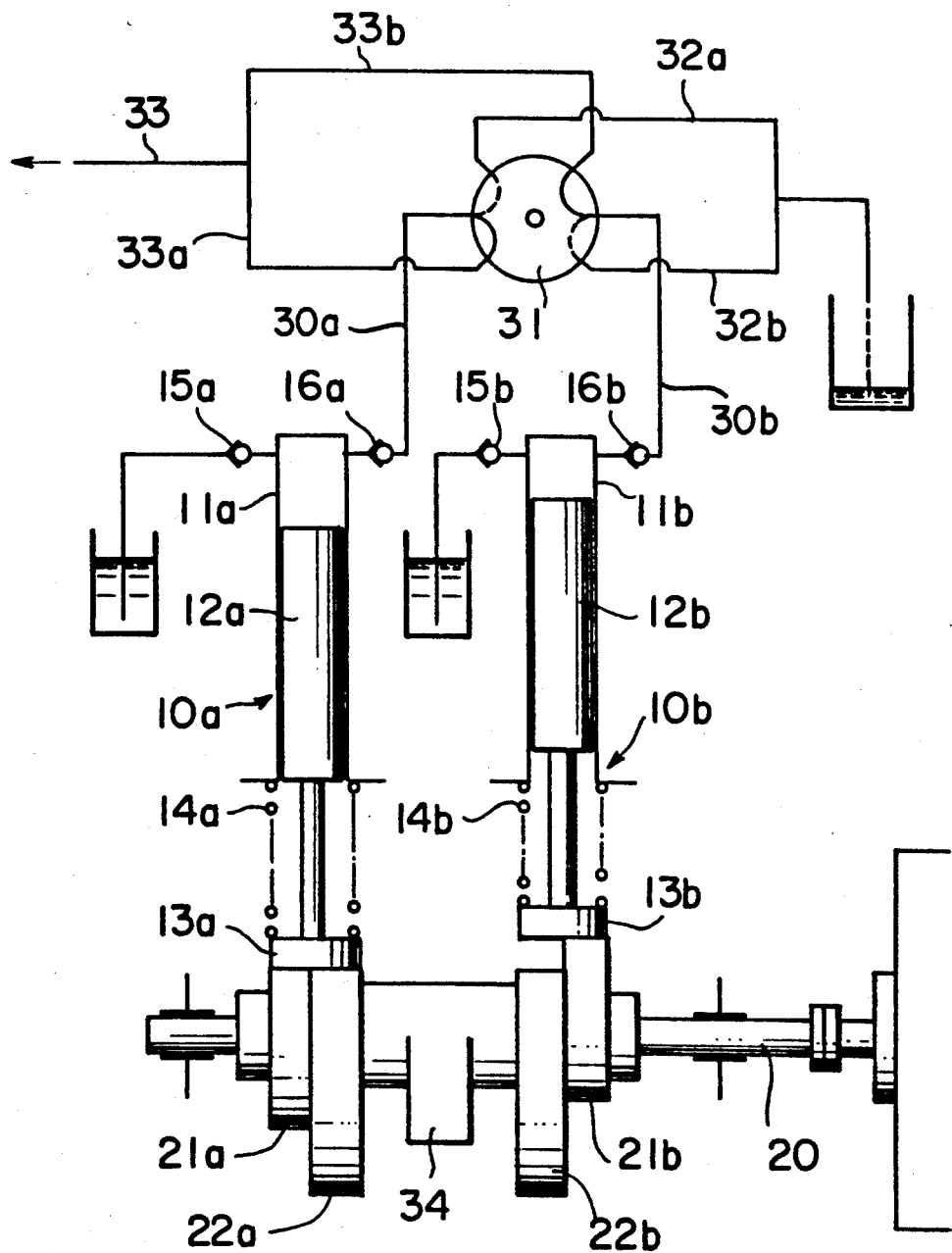
FIG. 1 is a schematic diagram showing the flow passages of the dual plunger pump system according to this invention.
Figure 2:
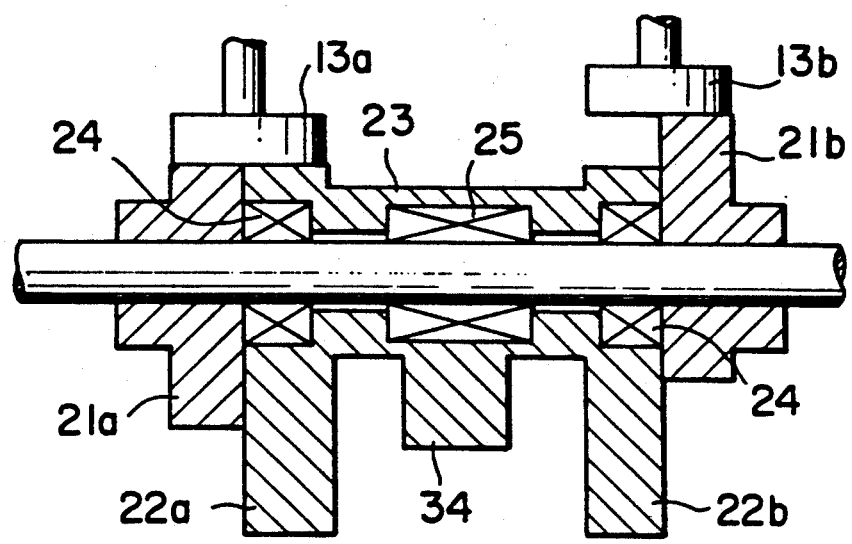
FIG. 2 is a sectional view showing the cam mechanism of the dual plunger pump system of this invention.

One embodiment of this invention will be described hereinafter with reference to the attached drawings FIG. 1 through FIG. 5.

In the drawings, reference numerals 10a and 10b denote plunger pumps, 11a and 11b denote cylinders, 12a and 12b denote plungers, 13a and 13b denote cam followers being in contact with the plungers through rods, 14a and 14b denote return springs for the plungers, 15a and 15b denote check valves on the intake sides of the pumps, and 16a and 16b denote check valves on the discharge sides of the pumps.

The plunger pumps 10a and 10b are operated by a cam mechanism driven by a rotary drive shaft 20. The cam mechanism is composed of a pair of short-stroke cams 21a and 21b opposite to the respective plungers 12a and 12b, and a pair of long-stroke cams 22a and 22b opposite to the plungers.

The short-stroke cams 21a and 21b each have a small difference between the minimum radius and the maximum radius thereof relative to the long-stroke cams 22a and 22b. The cam followers 13a and 13b are driven to reciprocate by the short-stroke cams 21a and 21b.

At the end of one reciprocating cycle of one of the plungers, the amount of fluid discharged from the pump driven by the plunger decreases. In the plunger pump system of this invention, at that time, the other plunger starts to reciprocate so as to maintain the amount of fluid discharged from the plunger pump constant. To be more specific, the shape and difference in reciprocating phase of the short-stroke cams 21a and 21b are so designed that, when the reciprocating plunger in the pump 10a nears its termination of one cycle of reciprocation, the plunger in the other pump 10b starts to reciprocate as shown in FIG. 4(A). That is, by effecting alternate reciprocations of the plungers, fluid can be discharged smoothly from the plunger pump system without pulsation of flowing as shown in FIG. 4(B).

Figure 3:
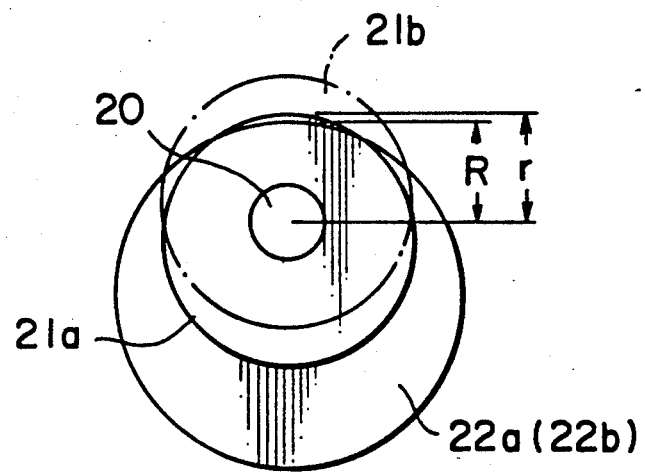
FIG. 3 is a side view showing the relation between the cams in the cam mechanism of this invention.
Figure 4:
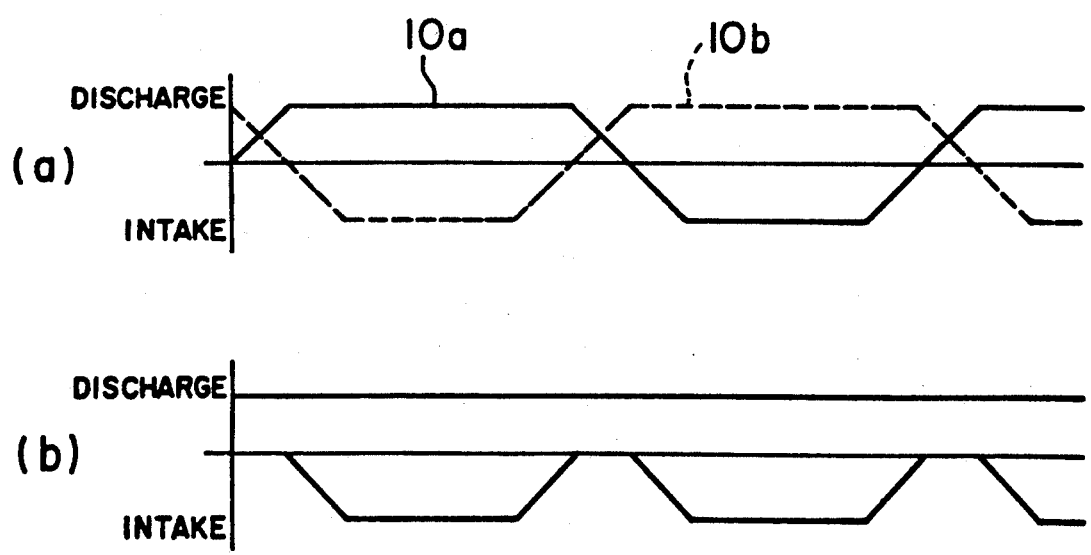
FIGS. 4(A) and 4(B) are a graph showing the fluid discharge and intake property when the short-stroke cams of the dual plunger pump system of this invention are operated simultaneously, and a graph showing the condition in which fluid is discharged by operating the short-stroke cams.
Figure 6:
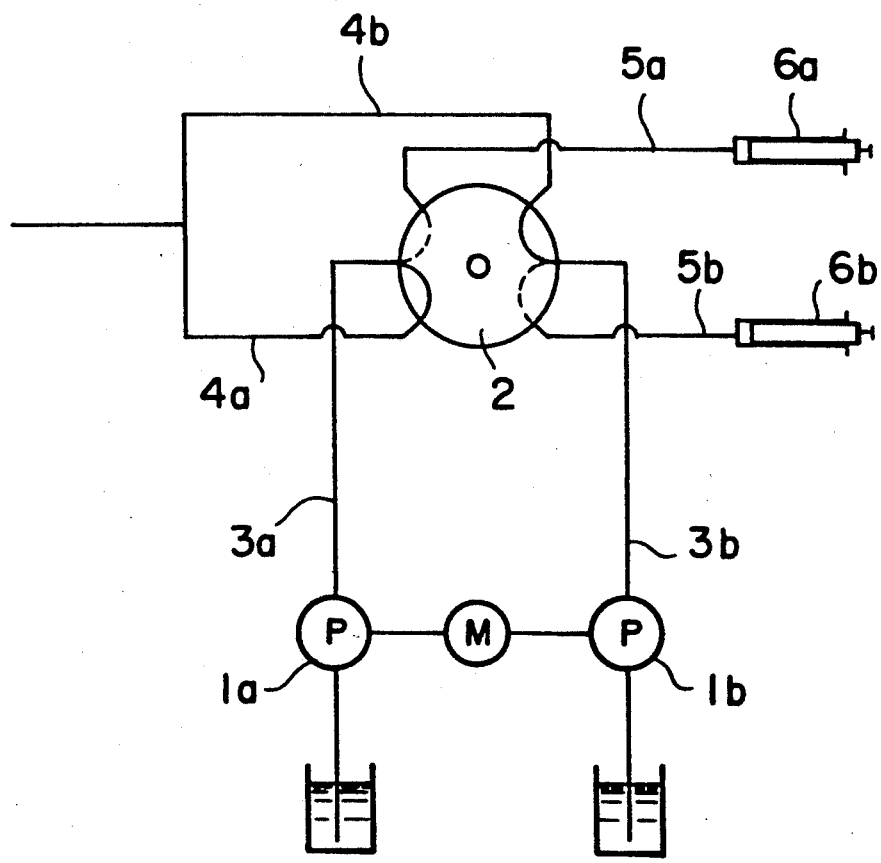
FIG. 6 is a schematic diagram showing the flow passages of the prior art dual plunger pump system.

On the other hand, the long-stroke cams 22a and 22b are integrally connected to the longitudinal end portions of the hollow shaft 23 and arranged at the substantially same angle. As shown in FIG. 3, the long-stroke cams 22a and 22b each have the minimum radius R smaller than the minimum radius r of the short-stroke cams 21a and 21b.

Figure 5:
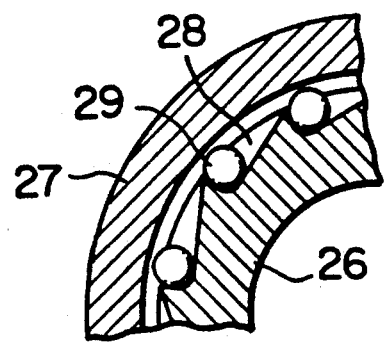
FIG. 5 is a sectional view showing in part the one-way clutch of the dual plunger pump system according to this invention.

The hollow shaft 23 is rotatably supported by the rotary drive shaft 20 through bearings 24. Between the hollow shaft 23 and the rotary drive shaft 20, there is disposed a one-way clutch 25 which permits the rotary motion of the rotary drive shaft 20 in one direction only to be transmitted to the hollow shaft 23. As shown in FIG. 5 as one example, the one-way clutch 25 may be formed by setting steel balls 29 in wedge-shaped spaces 28 defined between an inner race 26 and an outer race 27.

In the case of using the dual plunger pump system having the aforenoted structure for a fluid analyzer, the discharge side passages 30a and 30b of the plunger pumps 10a and 10b are connected to a change valve 31 as shown in FIG. 1 by way of example. The change valve 31 has a rotor which is rotatable for selectively connecting the discharge side passages 30a and 30b to either drain paths 32a and 32b or branch paths 33a and 33b.

In deaerating in the pumps 10a and 10b, the change valve 31 is first operated to connect the plunger pumps to the drain paths 32a and 32b as shown by the dotted lines in FIG. 1. Then, the rotary drive shaft 20 is rotated in the direction in which the rotary motion of the shaft 20 is transmitted to the long-stroke cams 22a and 22b through the one-way clutch 25, thereby driving the long-stroke cams 22a and 22b with a large stroke. As a result, fluids are introduced into the pumps through the check valves 15a and 15b and further sent out through the check valves 16a and 16b at a high speed, while removing air bubbles from the check valves 15a, 15b, 16a and 16b. Thus, exchange of fluid and cleansing in the fluid passages can also be readily and speedily carried out by operating the long-stroke cams 22a and 22b.

In a case of combining two kinds of fluids or feeding fluid to be analyzed, the long-stroke cams 22a and 22b are operated to fill the fluid passages with the fluid. Then, the rotary drive shaft 20 is rotated in the reverse direction to permit the one-way clutch 24 to run idle in such a state that the change valve 31 is positioned to connect the pumps to the branch paths 33a and 33b. The idling long-stroke cams 22a and 22b stop rotating in the state that the portion of the minimum radius R thereof is positioned upward due to the balance of weight. As a result, the short-stroke cams 21a and 21b operate the cam followers 13a and 13b, thereby driving the plungers 12a and 12b with a small stroke to alternately feed out the fluid little by little to the branch paths 33a and 33b.

The posture of the long-stroke cams 22a and 22b in racing the one-way clutch 24 can be ensured by forming a weight 34 on the hollow shaft 23.

As described in detail above, since the dual plunger pump system according to this invention has the short-stroke cams and long-stroke cams on the rotary drive shaft, which can be selectively operated by controlling the direction in which the rotary drive shaft rotates, scavenging and deaerating in the plunger pumps can be automatically carried out with high efficiency prior to the desired analysis of fluid, and even a very small amount of fluid can be sent out continuously at a high speed to be combined with another fluid.

Although the invention has been described in its preferred form with a certain degree of particularity, it is understood that the present disclosure of the preferred form has been changed in the details of construction and the combination and arrangement of parts may be resorted to without departing from the spirit and the scope of the invention as hereinafter claimed.

What is claimed is:

1. A dual plunger pump system comprising a pair of plunger pumps each consisting of a cylinder and a plunger disposed within said cylinder, an intake side passage with a check valve connected to each of said cylinders, a discharge side passage with a check valve connected to each of said cylinders, a pair or short-stroke cams for alternately operating said plungers, a rotary drive shaft for rotating said short-stroke cams, a pair of ling-stroke cams opposite to said respective plungers, and a one-way clutch disposed between said long-stroke cams and said rotary drive shaft and freely rotatable relative to said rotary drive shaft in a first direction of rotation of said drive shaft and is engaged for rotation with said drive shaft in a reverse direction of rotation of said drive shaft for simultaneously transmitting rotary motion of said drive shaft to said long-stroke cams only when said rotary drive shaft is rotated in said reverse direction of rotation.

2. The dual plunger pump system according to claim 1 wherein said discharge side passages are connected to a change valve having a rotor which is rotatable for selectively connecting said discharge side passages to either drain paths or branch paths.

* * * * *